(12) United States Patent
Cowin

(10) Patent No.: US 6,249,692 B1
(45) Date of Patent: Jun. 19, 2001

(54) METHOD FOR DIAGNOSIS AND MANAGEMENT OF OSTEOPOROSIS

(75) Inventor: Stephen C. Cowin, New York, NY (US)

(73) Assignee: The Research Foundation of City University of New York, New York, NY (US)

(*) Notice: Subject to any disclaimer, the term of this patent is extended or adjusted under 35 U.S.C. 154(b) by 0 days.

(21) Appl. No.: 09/641,634

(22) Filed: Aug. 17, 2000

(51) Int. Cl.⁷ ........................................................ A61B 5/00
(52) U.S. Cl. ............................ 600/407; 378/54; 600/410; 324/309
(58) Field of Search ........................................... 600/407, 410; 378/54; 382/128, 131, 132; 324/309

(56) References Cited

U.S. PATENT DOCUMENTS

| | | | |
|---|---|---|---|
| 3,847,141 | 11/1974 | Hoop | 128/2 V |
| 3,996,471 | 12/1976 | Fletcher et al. | 250/444 |
| 4,029,963 | 6/1977 | Alvarez et al. | 250/360 |
| 4,635,643 * | 1/1987 | Brown | 128/653 |
| 4,754,763 | 7/1988 | Doemland | 128/739 |
| 4,811,373 | 3/1989 | Stein | 378/54 |
| 5,247,934 | 9/1993 | Wehrli et al. | 128/653.2 |
| 5,259,384 | 11/1993 | Kaufman et al. | 128/660.01 |
| 5,270,651 * | 12/1993 | Wehrli | 324/308 |
| 5,368,044 | 11/1994 | Cain et al. | 128/739 |
| 5,426,709 | 6/1995 | Yoshida et al. | 382/132 |
| 5,651,363 | 7/1997 | Kaufman et al. | 128/660.02 |
| 5,772,592 | 6/1998 | Cheng et al. | 600/407 |
| 5,800,363 * | 9/1998 | Cheng et al. | 600/587 |
| 5,836,876 * | 11/1998 | Dimarogonas | 600/407 |
| 5,931,780 | 8/1999 | Giger et al. | 600/407 |
| 6,029,078 * | 2/2000 | Weinstein et al. | 600/407 |

OTHER PUBLICATIONS

Yang et al. "The Anisotropic Hooke's Law for Cancellous Bone and Wood" Journal of Elasticity, 53: pp. 125–146, 1999.

Siffert et al., "Dynamic Relationships of Trabecular Bone Density, Architecture, and Strength in a Computational Model of Osteopenia" Bone vol. 18, No. 2, pp. 197–206, Feb. 1996.

Luo et al., "Relationship Between Plain Radiographic Patterns and Three–dimensional Trabecular Architecture in The Human Calcaneus" Osteopors International 9: pp. 339–345, 1999.

Ott et al., "Ability of Four Different Techniques of Measuring Bone Mass to Diagnose Vertebral Fractures in Postmenopausal Women" Journal of Bone and Mineral Research, vol. 2, No. 3, pp. 201–210, 1987.

Cosman et al., "Radiographic Absorpitometry : A Simple Method for Determination of Bone Mass" Osteoporosis International 2 : pp. 34–38., 1991.

* cited by examiner

Primary Examiner—Marvin M. Lateef
Assistant Examiner—Eleni Mantis Mercader
(74) Attorney, Agent, or Firm—Dykema Gossett PLLC

(57) ABSTRACT

Non-invasive quantitative evaluation of biomechanical properties of bone in a bony locale in a living body as manifested by one or more of the quantities: a set of anisotropic elastic constants, strength, or fracture risk is performed by measuring a bone mineral density and a trabecular grain at the bony locale. The measurements of bone mineral density and a trabecular grain are processed using a univariate nonlinear regression to obtain the set of anisotropic elastic constants. In an alternative embodiment, the strength of a bone in a bony locale is evaluated through the use of a three-dimensional strength surface.

7 Claims, 2 Drawing Sheets

METHOD FOR DIAGNOSIS AND MANAGEMENT OF OSTEOPOROSIS

BACKGROUND OF THE INVENTION

The invention pertains to a method for non-invasively and quantitatively evaluating the biomechanical status of bone at a specific locale or set of locales in vivo at a given time, where the biomechanical status is characterized quantitatively in terms of a set of elastic constants, bone strength and/or fracture risk.

In recent years, various attempts have been made to use diverse forms of energy to assess the condition of bone tissue in vivo. The primary means utilized presently involves the application of ionizing radiation, namely x-rays. These x-ray-based methods, while providing reasonable estimates of bone-mineral density, do not accurately distinguish individuals with respect to risk of osteoporotic bone fracture. This is due, in part at least, to the dependence of bone biomechanical properties on architectural or structural features, aspects, which are not captured in bone-mineral density measurements alone. In this regard, it should be noted that the architectural features refer primarily to the microstructure of the trabecular portion of a bone. It is this trabecular portion that provides the majority of the biomechanical strength and stiffness in many bones, which are involved in osteoporosis, such as the hip and vertebrae.

As noted, the primary means for assessing bone is to determine bone-mineral density with ionizing electromagnetic radiation, i.e. x-rays. A review of these radiation-based methods may be found in the article by Ott et al., in the *Journal of Bone and Mineral Research,* Vol. 2, pp. 201–210, 1987. These techniques all operate on the basic principle that the attenuation of an x-ray beam depends on the amount of bone present at a particular anatomical site in a subject's body, and that this attenuation (and therefore some information on the amount of bone present) can be evaluated. Several techniques exist for performing this type of densitometric measurement, such as single photon absortiometry (SPA), dual photon absortiometry (DPA), single energy x-ray absortiometry (SXA), dual energy x-ray absorptiometry (DXA), and quantitative computed tomography (QCT). A related but simpler bone density estimation method, known as radiographic densitometry (RA), has also been described (see, for example the 1991 publication by F. Cosman, B. Herrington, S. Himmelstein and R. Lindsay entitled "Radiographic Absorptiometry: A Simple Method for Determination of Bone Mass," in *Osteoporosis International,* Volume 2, pp. 34–38.) This technique, based on a plain radiograph, is applicable to appendicular sites only; it has mostly been applied to evaluation of the bone mineral density of the phalanges (fingers). It utilizes digital image processing to process a plain radiograph that was obtained with an aluminum alloy reference step wedge placed adjacent to the hand.

Acoustic techniques have also been utilized for non-invasive bone assessment, including for example, both ultrasonic and low-frequency vibrational methods. Although these techniques have the potential for providing a great deal of information on bone density and strength, they have not yet become widely used for in vivo bone assessment. Some reasons for this are that the techniques are highly sensitive to positioning and coupling of the acoustic transducers and are also affected by soft tissue overlying the bone.

Yoshida, et al., U.S. Pat. No. 5,426,709, discloses a plain x-ray measurement method and apparatus for evaluating bone mineral density of a bone, upon determination of quantity level of light that transmits through the x-ray film. The Yoshida, et al. device adjusts the light intensity level so that it is within a predetermined quantity range of light, in comparison to that which is transmitted through an aluminum step wedge. A temperature compensation for an output from the transmitting light detecting unit, i.e., a charge coupled device image sensor, is carried out by utilizing a light shielded output from the sensor.

U.S. Pat. No. 4,811,373 to Stein discloses a device to measure bone density. In the invention, Stein describes an x-ray tube operating at two voltages to generate a pencil beam, together with an integrating detector. The detector measures the patient-attenuated beam at the two energy levels (known commonly as dual energy x-ray absorptiometry) of the pencil beam. Calibration is accomplished by a digital computer on the basis of passing the pencil beam through a known bone-representing substance as the densitometer scans portion of the patient having bone and adjacent portions having only flesh.

Fletcher et al., in U.S. Pat. No. 3,996,471, disclose another dual energy x-ray absorptiometry method. In this invention, a target section of a living human body is irradiated with a beam of penetrative radiations of preselected energy to determine the attenuation of such beam with respect to the intensity of each of two radiations of different predetermined energy levels. The resulting measurements are then employed to determine bone mineral content.

Alvarez et al., in U.S. Pat. No. 4,029,963, disclose a method for decomposing an x-ray image into atomic-number-dependent and density-dependent projection information. The disclosed technique is based on the acquisition of x-ray images from the low and high energy regions, respectively.

Kaufman et al., U.S. Pat. Nos. 5,259,384 and 5,651,363, disclose method and apparatus for ultrasonically assessing bone tissue. In the first of the two Patents, a composite sine wave acoustic signal consisting of plural discrete frequencies within the ultrasonic frequency range to 2 MHz are used to obtain high signal-to-noise ratio of the experimental data. A polynomial regression of the frequency-dependent attenuation and group velocity is carried out, and a nonlinear estimation scheme is applied in an attempt to estimate the density, strength, and fracture risk of bone in vivo. In the second of the two Patents, a parametric modeling approach is used in a comparative analysis for assessment of bone properties.

U.S. Pat. No. 3,847,141 to Hoop discloses a device to measure bone density as a means of monitoring calcium content of the involved bone. A pair of opposed ultrasonic transducers is applied to opposite sides of a patient's finger, such that recurrent pulses transmitted via one transducer are "focused" on the bone, while the receiving response of the other transducer is similarly "focused" to receive pulses that have been transmitted through the bone. The circuitry is arranged such that filtered reception of one pulse triggers the next pulse transmission; the filtering is by way of a bandpass filter, passing components of received signals, only in the 25 to 125 kHz range; and the observed frequency of retriggering is said to be proportional to the calcium content of the bone.

Doemland, U.S. Pat. No. 4,754,763, discloses a noninvasive system for testing the integrity of a bone in vivo. He uses low-frequency mechanical vibrations to characterize the state of healing in a fractured bone. The frequency response is used to classify the stage of healing.

Cain et al., U.S. Pat. No. 5,368,044, applied a similar method, namely, low-frequency mechanical vibrations, to assess the state or stiffness of bone in vivo. The method evaluates the peak frequency response or a cross-correlation of the frequency vs. amplitude response.

Cheng et al., U.S. Pat. No. 5,772,592, disclosed a method for diagnosing and monitoring osteoporosis, using volumetric bone density and cross-sectional area information in a patient.

Wehrli et al., U.S. Pat. No. 5,247,934, disclosed a method for diagnosing osteoporosis with magnetic resonance imaging. In their approach, a measure of trabecular thickness and bone perimeter, determined from magnetic resonance imaging, are used together to assess the condition of trabecular bone at the site of interest.

The prior art, exemplified by the references that have been briefly discussed, have had little success in providing an accurate determination of the biomechanical state of a bone in a living body. They have focussed primarily on x-ray bone densitometric techniques, such as dual energy methods, which provide measures of bone-mineral density only, which is limited in terms of its relation to bone elasticity, strength and fracture risk. On the other hand, acoustic (low-frequency vibrational or ultrasonic) means have not yet produced an accurate practical method for clinical bone assessment either.

Of great utility in the field of bone assessment would be a technique which could provide accurate assessment of the biomechanical properties of bone in vivo, but without significant additional complexity as compared to that associated with x-ray bone densitometers, such as offered by dual energy x-ray absorptiometry.

BRIEF STATEMENT OF THE INVENTION

It is accordingly an object of the invention to provide an improved method and apparatus for non-invasive and quantitative evaluation of bone tissue in vivo.

Another object is to meet the above object, such that the biomechanical properties of bone may be readily and more reliably quantitatively evaluated than heretofore.

A specific object is to achieve the above objects in such a way that an estimate of bone biomechanical properties can be obtained that intrinsically includes the effects of architecture.

A further specific object is to determine the biomechanical properties of bone in vivo, wherein the biomechanical properties are reflected in a set of anisotropic elastic constants, bone strength, or fracture risk.

A specific object is to achieve the above objects substantially with conventional and widely available biomedical equipment.

Briefly stated, the invention in its presently preferred form achieves the foregoing objects by subjecting an individual to a high resolution magnetic resonance scan. This scan is used to obtain a high resolution magnetic resonance three-dimensional (3D) image of a bone at a bony locale, i.e., at an anatomical site, in a living body. In this embodiment the preferred bony locale is the hip (i.e., the proximal femur). The obtained 3D image is then processed to obtain a measure of the bone-mineral density of a region-of-interest of the proximal femur. This bone-mineral density is measured in terms of grams per cubic centimeter. The image is then further processed using mean intercept length, to obtain, at the same region-of-interest, a principal-grain direction. The principal-grain direction is the primary direction of orientation of the bone trabeculae, and is also coincident with the primary direction of load-bearing in the bone. Finally, the bone-mineral density and the principal-grain direction are processed, using univariate nonlinear regressions, whereby to obtain a quantitative measure of the biomechanical state of the bone, that is, a set of seven (7) independent anisotropic elastic constants associated with the bone at the given anatomical site.

BRIEF DESCRIPTION OF THE DRAWINGS

The invention will be described in detail for a presently preferred embodiment, in conjunction with the accompanying drawings, in which.

DETAILED DESCRIPTION OF THE INVENTION

The invention will be described in detail for a presently preferred embodiment, in conjunction with the accompanying drawings.

Figure 1:
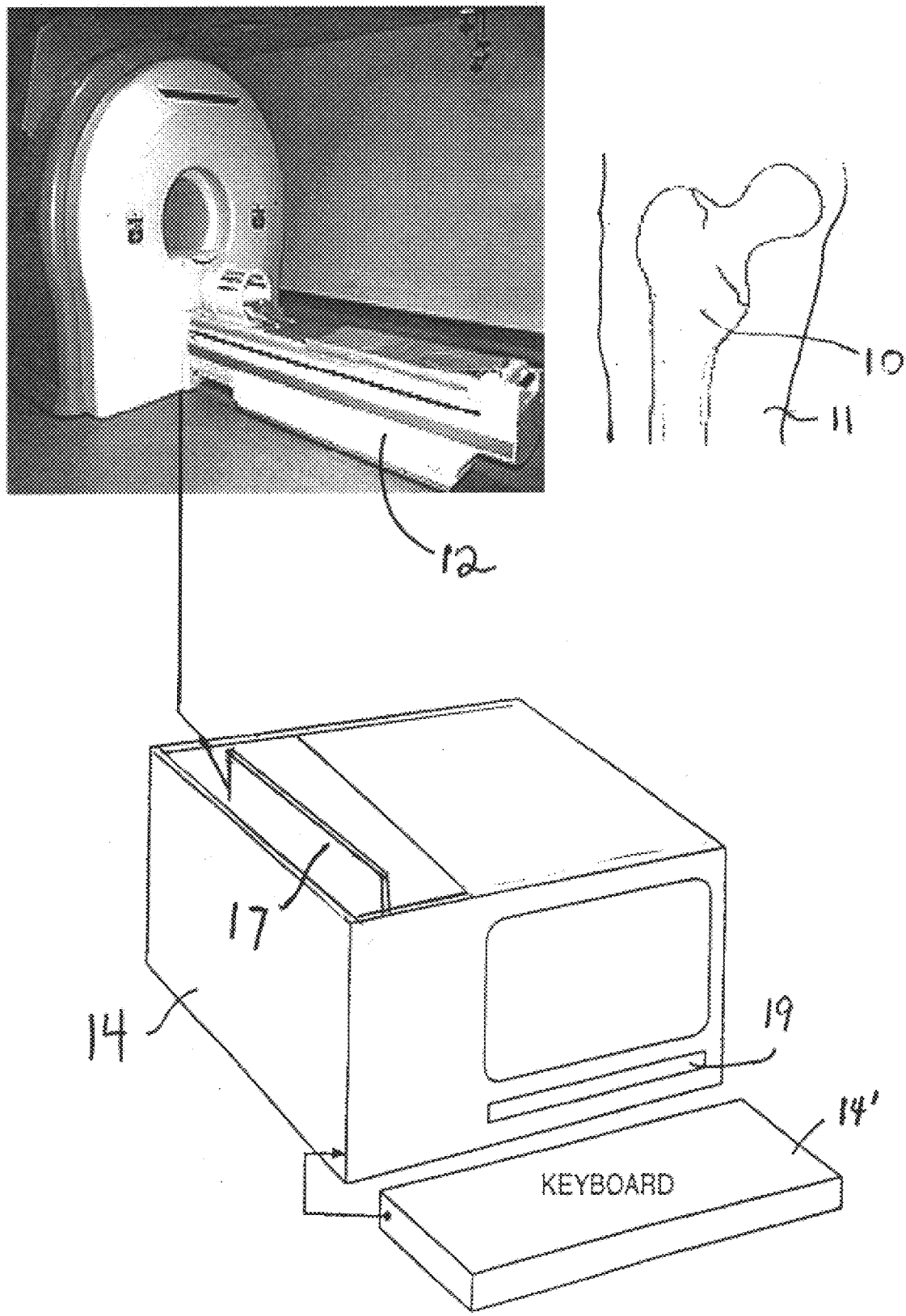
FIG. 1 is a schematic diagram showing the components of a presently preferred embodiment of the invention.

The invention is shown in FIG. 1 in application to interconnected components for constructing apparatus for performing methods of the invention, namely, for non-invasively and quantitatively evaluating the biomechanical properties of bone in vivo at a given anatomical site, namely the anisotropic elastic constants, bone strength or fracture risk, at a given time. These components are commercially available from different sources and will be identified before providing detailed description of their total operation.

In FIG. 1, the bone 10 to be analyzed in a bony locale of a body is shown surrounded by soft tissue 11 and to be inserted into a magnetic resonance scanner 12. The magnetic resonance scanner may suitably be the MAGNETOM Symphony 1.5T, available from Siemens Corporation of Munich, Federal Republic of Germany. As shown, magnetic resonance scanner 12 is used to produce non-invasively a three-dimensional image of the bone 10. In the presently preferred embodiment of the invention, bone 10 is the proximal femur, i.e., the hip bone.

With reference again to FIG. 1, processing of data is governed by computer means 14, which may be a PC computer, such as the Model 800 available from Gateway, Inc., North Sioux City, S. Dak.; as its designation suggests, this computer contains an 800 MHz clock-pulse generator, and an Intel Pentium III processor, with provision for keyboard instruction at 14'. The magnetic resonance scanner 12 is interfaced to the personal computer 14, which allows for the transfer to the computer of all the image data via computer interface 17 for processing, storage and display.

Finally, general signal-processing/display/storage software, for the signal-processing/image-processing control and operation of the computer is not shown but will be understood to be a CD-ROM loaded at 19 into the computer; this software is suitably the MATLAB for Windows, available from The Math Works, Inc., Natick, Mass. This software includes the Image Processing, Optimization and Signal Processing Toolboxes. Further software, also not shown but loaded into the computer, is least-squares regression modeling software, identified as TableCurve, a product of Jandel Scientific, Inc., San Rafael, Calif., a Fortran language compiler and a Visual C++ language compiler, both available from Microsoft Corporation, Beaverton, Oreg. In the presently preferred embodiment, involving the described components of FIG. 1, the computer will be understood to be further programmed to generate estimates of bone-mineral density, principal-grain direction, and of the above-indicated and currently analyzed bone property, namely, biomechanical property, as manifested through one or more of the following: anisotropic elastic constants, bone strength and fracture risk.

Figure 2:
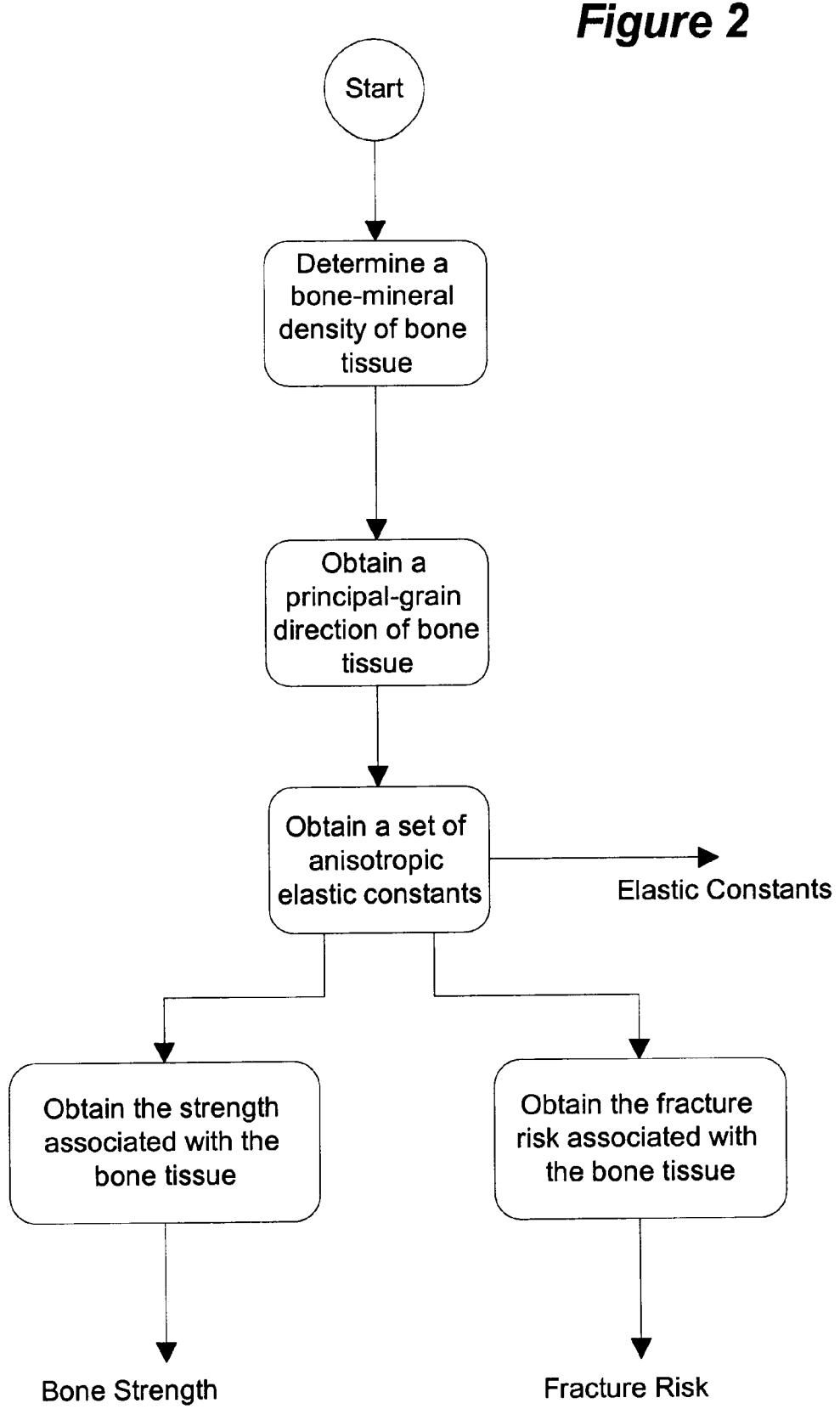
FIG. 2 is a flow chart of computer-controlled operations of the invention, in automatically analyzing and quantitatively reporting an estimate of the biomechanical properties of bone mineral density.

In the presently preferred embodiment of the invention and with additional reference to the flow diagram of FIG. 2, a bone 10 and its surrounding soft tissue 11 within a living body (not shown) are subjected to a high resolution magnetic resonance scan from scanner 12. The 3D image is then transferred to computer 14 via the computer interface 17.

In the presently preferred embodiment of the invention, the 3D image is processed to obtain an estimate of the bone-mineral density. This is achieved by first segmenting a selected region-of-interest of the image into bone and marrow (also known as "void") regions, using a local thresholding procedure. Such thresholding techniques are well known in the art; a specific one which is used in the present embodiment is described in the article by G. M. Luo et al., "Relationship of plain radiographic patterns to three-dimensional trabecular architecture in the human calcaneus," in *Osteoporosis International*, Volume 9:, pp. 339–345, 1999, which is incorporated by reference hereinto. Following thresholding and segmentation, bone-mineral density is calculated by "counting up" the number of voxels (volume elements) in the region-of-interest which are segmented into bone, and dividing by the total number of voxels within the region-of-interest, which includes both bone voxels and marrow voxels. The result of this computation is the bone volume fraction (a number between 0 and 1), which represents the fraction of the volume in the region-of-interest which is composed of bone, which is then multiplied by the volumetric density of bone tissue per se, $\rho_b$, to obtain the bone-mineral density, in grams per cubic centimeter, of the bone within the region of interest at the given anatomical site. In the presently preferred embodiment, $\rho_b=1.85$ g cm$^{-3}$, which is the value given by the International Commission on Radiological Protection (ICRP), as noted in Appendix B2 and B3 of the book entitled *Introduction to Radiological Physics and Radiation Dosimetry* by Frank H. Attix, published by Wiley Interscience in New York in 1986, and which is incorporated by reference hereinto. Following determination of the bone-mineral density, the segmented 3D image is further processed to obtain the principal grain direction. The principal grain direction is the main direction or main orientation of the trabeculae in the bone at the region-of-interest. In this embodiment, the principal grain direction is evaluated by computing the mean intercept length in three dimensions, wherein the mean intercept length in any given direction is defined as the inverse of the number of intersections per unit length of a test line with the bone-void boundary. The principal grain direction is the direction in which the mean intercept length is maximum. Several publications describe in greater detail the meaning of trabecular grain and methods used to measure it. They are "The anisotropic Hooke's Law for cancellous bone and wood", by G. Yang et al., in the *Journal of Elasticity*, Vol. 53, pp. 125–146 in 1999; "Dynamical relationships of trabecular bone density, architecture and strength in a computational model of osteopenia", by R. S. Siffert et al., in *Bone*, Vol. 18, No. 2, pp. 197–206, in 1996; and "The quantitative morphology of anisotropic trabecular bone," by W. J. Whitehouse, in the *Journal of Microscopy*, Vol. 101, pp. 153–168, in 1974, all three of which are incorporated by reference hereinto.

Once both the bone-mineral density and principal trabecular grain associated with the bone tissue at the bony locale of the body are obtained, a set of anisotropic elastic constants are evaluated. In the presently preferred embodiment of the invention, the set of anisotropic elastic constants are comprised of 5 independent constants and are obtained by processing the bone-mineral density and principal trabecular grain with nonlinear univariate regressions. The anisotropic elastic constants are computed, that is, the bone-mineral density and principal grain direction are processed according to the equations similar to the following:

$$E_1=E_2=1000E_t\rho^2 GPa \tag{1a}$$

$$E_3=3072E_t\rho^2 GPa \tag{1b}$$

$$G_{23}=G_{13}=863E_t\rho^2 GPa \tag{1c}$$

$$G_{12}=410E_t\rho^2 GPa \tag{1d}$$

$$\nu_{21}=\nu_{12}=0.264 \tag{1e}$$

$$\nu_{32}=\nu_{31}=0.650 \tag{1f}$$

$$\nu_{23}=\nu_{13}=0.210 \tag{1g}$$

The set of five (5) independent anisotropic elastic constants in Eq. 1 are given by the set $\{E_1, E_3, G_{23}=G_{13}, \nu_{21}=\nu_{12},$ and $\nu_{32}=\nu_{31}\}$; it can be shown that $G_{12}$ and $\nu_{23}=\nu_{13}$ are dependent upon the first five. In the presently preferred embodiment, the principal grain direction is notated by subscript "3," thus, $E_3$ is the elastic stiffness associated with the principal grain direction. It should be understood that in the presently preferred embodiment of the invention the measurement of the principal grain direction is used to determine the value of, and the direction associated with, the largest elastic stiffness, $E_3$, as well as of the remaining 4 independent elastic constants.

The above embodiment of the invention has relied on an important insight by the present inventor, namely the concept of trabecular grain and the role that it plays in understanding the biomechanics of trabecular bone. Thus it is useful to describe herein some additional details on this concept. The trabecular grain is defined in analogy with the idea of the grain of wood, but the definition is more precise, as it well might be made for wood. The symmetry of (linearly elastic) materials may be characterized by the number and orientation of the planes of mirror, or reflective symmetry. A plan of mirror symmetry is like the plane of a mirror, everything is reflected, but the left to right structures are imaged in the mirror as right to left structures. The material symmetry of wood is an interesting example; it has three perpendicular planes of mirror symmetry. One plane is perpendicular to the long axis of the tree trunk, another is perpendicular to the tangent to the growth ring, and the third is perpendicular to the radial direction associated with the growth rings. For wood, the grain of the wood generally means the direction coincident with the long axis of the tree trunk. However, if the wood grain is defined as trabecular grain is defined, the wood grain would be a set of three orthogonal, ordered directions, the first one of which lies along the long axis of the tree trunk, which is locally the stiffest direction, the second and third directions are directions orthogonal to each other in the plane perpendicular to the long axis of the tree trunk and represent the second and third stiffest directions in the local region of the wood. The existence of these three perpendicular planes of mirror symmetry, and no others, mean that wood has orthotropic material symmetry.

The phrase "trabecular grain" is employed herein in direct analogy with the above rigorous concept of "wood grain."

Trabecular grain means a set of three ordered orthogonal directions, the first one of which lies along the local predominant trabecular direction (what was termed "principal grain direction," hereinabove), which is locally the stiffest direction; the second and third directions are directions orthogonal to each other in the plane perpendicular to the first direction and represent the second and third stiffest directions in the local region of the cancellous bone. It should be appreciated that these directions are orthogonal because it has been shown that cancellous bone has orthotropic elastic symmetry, that is to say, three perpendicular planes (or, alternatively, axes) of mirror or reflective symmetry, in each local region of the bone tissue. In certain instances it is possible to assume that trabecular bone can be described adequately, from a biomechanical perspective, by only five (5) independent elastic constants (that is, that it may be characterized as an a transversely isotropic material). This is the case of the preferred embodiment disclosed supra.

It is useful to provide also some additional details related to the relationships of the elastic constants which underlie the invention disclosed herein. In 1676 Hooke noted the proportionality between the loading applied to a solid specimen and the resulting elongation of the specimen; Hooke's law is now expressed as a linear relationship between stress and strain. The dependence of the anisotropic Hooke's law upon a reference coordinate system is important to note. For an arbitrary reference coordinate system it takes a form in which, in general, each one of the strain components $E_{11}$, $E_{22}$, $E_{33}$, $E_{23}$, $E_{13}$ and $E_{12}$ is linearly related to each one of the stress components $T_{11}$, $T_{22}$, $T_{33}$, $T_{23}$, $T_{13}$ and $T_{12}$. (In this situation all the elements in the matrix (Eq. 3) below would be non-zero, in general.) The form of the anisotropic Hooke's law for an orthotropic elastic solid relates the three normal strain components $E_{11}$, $E_{22}$ and $E_{33}$ to the three normal stress components $T_{11}$, $T_{22}$ and $T_{33}$ by $$E_{11}=(1/E_1)(T_{11}-\nu_{21}T_{22}-\nu_{31}T_{33}), E_{22}=(1/E_2)(-\nu_{12}T_{11}+T_{22}-\nu_{32}T_{33}),$$
$$E_{33}=(1/E_3)(-\nu_{13}T_{11}-\nu_{23}T_{22}+T_{33}), \quad (2a)$$

and the three shearing strain components $E_{23}$, $E_{13}$ and $E_{12}$ to the three shearing stress components $T_{23}$, $T_{13}$ and $T_{12}$ by $$E_{23}=T_{23}/2G_{23}, E_{13}=T_{13}/2G_{13}, E_{12}=T_{12}/2G_{12}. \quad (2b)$$

The elastic coefficients in Hooke's law (Eq. 2) are the three Young's moduli $E_1$, $E_2$ and $E_3$ in the three perpendicular coordinate directions, the six Poisson ratios denoted by subscripted v's (only three of the six Poisson ratios are independent since $\nu_{12}/E_1=\nu_{21}/E_2$, $\nu_{13}/E_1=\nu_{31}/E_3$ and $\nu_{23}/E_2=\nu_{32}/E_3$), and the three shear moduli $G_{23}$, $G_{13}$ and $G_{12}$. A particular coordinate system in the material was selected to obtain the representation (Eq. 2) for Hooke's law for an orthotropic elastic solid. This coordinate system was selected so that each of the three perpendicular coordinate directions is the normal to one plane of a set of three perpendicular planes of mirror or reflective symmetry that characterize elastic orthotropic symmetry. This special coordinate system coincides with the "trabecular grain" described hereinabove.

In the case of isotropic symmetry all the Young's moduli are equal, $E_1=E_2=E_3=E$; all the shear moduli are all equal, $G_{23}=G_{13}=G_{12}=G$; all the Poisson ratios are equal to $(E/2G)-1\_(2)$; and the equations (Eq. 2) satisfying these equalities represent Hooke's law for isotropic symmetry. The isotropic form of Hooke's law has the same form in all coordinate systems because, for isotropic symmetry, all directions are normals to planes of mirror or reflective symmetry, not just the three coordinate planes in one reference coordinate system as is the case for orthotropic symmetry.

The orthotropic elastic coefficients, $1/E_1$, $-\nu_{12}/E_1$, $-\nu_{13}/E_1$, $-\nu_{21}/E_2$, $1/E_2$, $-\nu_{23}/E_2$, $-\nu_{31}/E_3$, $-\nu_{32}/E_3$, $1/E_3$, $1/2G_{23}$, $1/2G_{13}$ and $1/2G_{12}$ may be considered either as the components of a fourth rank tensor in a space of three dimensions or as a second rank tensor in a space of six dimensions. The matrix of six-dimensional second rank tensor components is:

$$\begin{bmatrix} 1/E_1 & -\nu_{12}/E_1 & -\nu_{13}/E_1 & 0 & 0 & 0 \\ -\nu_{12}/E_2 & 1/E_2 & -\nu_{23}/E_2 & 0 & 0 & 0 \\ -\nu_{13}/E_3 & -\nu_{32}/E_3 & 1/E_3 & 0 & 0 & 0 \\ 0 & 0 & 0 & 1/2G_{23} & 0 & 0 \\ 0 & 0 & 0 & 0 & 1/2G_{13} & 0 \\ 0 & 0 & 0 & 0 & 0 & 1/2G_{12} \end{bmatrix} \quad (3)$$

It should be appreciated that the eigenvectors and eigenvalues of this matrix may be calculated from the numerical values of the orthotropic elastic coefficients using standard contemporary mathematical analysis programs such as MathCad, MATLAB, Maple, Mathematica or MacSyma. MATLAB is most suitably used in the present embodiments of the invention, and is available from The MathWorks, Inc., Natick, Mass.

Invariants of tensorial quantities are scalars that are independent of the reference coordinate system used for the tensor components. A simple example of an invariant is the magnitude of a vector. A vector is a first rank tensor. The sum of the squares of the components of a vector is an invariant because it is equal to the square of the length of the vector and the length of the vector is the same in all Cartesian coordinate systems. For a second rank tensor in three dimensions, like the stress or strain tensor, there are three well known invariants. The three eigenvalues of the matrix of the tensor components are an irreducible set of invariants, although that is not the customary set of invariants employed. The equivalent customary set of invariants employed consists of combinations of the eigenvalues. The first invariant is the sum of three eigenvalues, the third invariant is the product of the three eigenvalues and the second invariant is the sum of the set of all products of the three eigenvalues taken two at a time. For the second rank tensor in a space of six dimensions, there are eighteen invariants—one set of which are the six eigenvalues and twelve functions of the six, six-dimensional eigenvectors. Thus the invariants of the matrix of six-dimensional second rank tensor components given above may be calculated from their numerical values using standard contemporary mathematical analysis programs.

A geometrically appealing and potentially utilitarian formulation of the anisotropic form of the linear Hooke's law can be described as follows. The eigenvectors of the three-dimensional fourth-rank anisotropic elasticity tensor, considered as a second-rank tensor in a six-dimensional space, are called eigentensors when projected back into the three-dimensional space. The maximum number of eigentensors for any elastic symmetry is therefore six. The concept of an eigentensor was first introduced by Kelvin who called eigentensors "the principal types of stress or of strain." The eigentensors for a linear isotropic elastic material are well known in the art. They are the deviatoric second-rank tensor and a tensor proportional to the unit tensor, the spherical or hydrostatic or dilatational part of the tensor. Explicit forms of the eigentensors for all of the linear elastic symmetries except monoclinic and triclinic symmetry are also known in the art. The Kelvin formulation shows that six distinct modes of deformation, each characterized by a single Kelvin elastic modulus, are possible in an arbitrary linear elastic anisotropic material. These six modes consist of three dilatational (volume changing) strain modes and three isochoric (volume preserving) shear modes for a material with orthotropic symmetry. The three dilatational strain modes are simply different linear combinations of the three normal strains associated with the three symmetry axes of the orthotropic material. Each of these three deformation modes can be viewed as a cube being deformed into a rectilinear parallelepiped; each pair of sides of the rectilinear parallelepiped can be either compressed towards one another or extended apart from one another relative to the same pair of sides of the original cube. The mode must be dilatational if all three pairs of sides of the parallelepiped are either all compressed towards one another or all extended apart from one another relative to the pairs of sides of the original cube. The mode will be isochoric if two pairs of sides of the parallelepiped are compressed towards one another and the third pair is extended apart from one another, or vice versa, relative to the pairs of sides of the original cube, as long as there is no volume change. Each of the three shear deformation modes is an isochoric shearing deformation in which the typical shearing plane and typical plane of shear are both planes of symmetry of the orthotropic material. In the special case of isotropy these six deformation modes are reduced to two by maintaining one distinct dilatational strain mode and having the other two distinct dilatational strain modes coalesce with the three shear modes into one isochoric extension-contraction-shearing deformation mode of multiplicity five. For the isotropic material these modes are well known; the distinct mode is called the dilatational strain mode, and the multiplicity five isochoric extension-contraction-shearing deformation mode is called the deviatoric strain mode. The single Kelvin modulus for the dilatational strain mode is three times the bulk modulus k, k=GE/(9G−3E), and the single Kelvin modulus for the deviatoric strain mode is twice the shear modulus, G.

For trabecular human bone the strain-stress relations are given by $$E_{11}=\{1/\rho^2 E_t\}\{(T_{11}/760)-0.385(T_{22}/1458)-0.749(T_{33}/3072)\}.$$

$$E_{22}=\{1/\rho^2 E_t\}\{-0.200(T_{11}/760)+(T_{22}/1458)-0.547(T_{33}/3072)\},$$

$$E_{33}=\{1/\rho^2 E_t\}\{-0.185(T_{11}/760)-0.260(T_{22}/1458)+(T_{33}/3072)\},$$

$$E_{23}=\{1/\rho^2 E_t\}\{T_{23}/1065\},\ E_{13}=\{1/\rho^2 E_t\}\{T_{13}/726\},\ E_{12}=\{1/\rho^2 E_t\}\{T_{12}/445\}. \tag{4}$$

The representation in Eq.(4) of the elastic coefficients for human bone is quite interesting and contains revealing insights. Perhaps the most interesting insight is that the anisotropy is reflected mainly in the Young's modulus and only to a minor extent in the shear moduli and the Poisson ratios.

From a clinical viewpoint the insights provided hereinabove suggest that more information concerning cancellous bone competence can be extracted from DXA data and textbook data on local cancellous bone structure (i.e., the primary direction of trabecular grain data). From a biomechanics perspective the model provides the much more accurate representations of the elastic coefficients of cancellous bone achieved heretofore.

The proposed enhancement of the evaluation of a person's risk for osteoporosis would be based on a knowledge of the local cancellous bone volume fraction or bone mineral density, and a knowledge of the anatomically established, (whether measured at the time or previously recorded), trabecular grain. These data would be combined using the method described herein to evaluate the anisotropic elastic constants, strength, or fracture risk in a local cancellous bone.

In another embodiment of the invention, the entire set of 12 orthotropic elastic constants are obtained. In this case, three orthogonal directions of trabecular grain are obtained.

$$E_1=760E_t\rho^2 GPa \tag{4a}$$

$$E_2=1458E_t\rho^2 GPa \tag{4b}$$

$$E_3=3072E_t\rho^2 GPa \tag{4c}$$

$$G_{23}=1065E_t\rho^2 GPa \tag{4d}$$

$$G_{13}=726E_t\rho^2 GPa \tag{4e}$$

$$G_{12}=445E_t\rho^2 GPa \tag{4f}$$

$$v_{23}=0.260 \tag{4g}$$

$$v_{32}=0.547 \tag{4h}$$

$$v_{13}=0.185 \tag{4i}$$

$$v_{31}=0.749 \tag{4j}$$

$$v_{12}=0.200 \tag{4k}$$

$$v_{21}=0.385 \tag{4l}$$

The set of nine (9) independent anisotropic elastic constants in Eq. 4 are given by the set $\{E_1, E_2, E_3, G_{23}, G_{13}, G_{12}, v_{12}, v_{13} \text{ and } v_{23}\}$; it can be shown that $v_{21}$, $v_{31}$ and $v_{32}$ are dependent upon the first nine. In the presently preferred embodiment, the principal grain direction is notated by subscript "3," thus, $E_3$ is the elastic stiffness associated with the principal grain direction.

In the prior two embodiments of the invention, sets of anisotropic elastic constants associated with a bone at a given anatomical site in a living body were determined. Since for bone, the elastic constants are closely correlated to its strength, estimates of strength values can also be achieved. In one such alternative embodiment, a closed three-dimensional strength surface is obtained from a set of anisotropic elastic constants, which are assumed to be linearly related to values of strength. The closed three-dimensional surface is further processed to determine a quantitative measurement of strength of the bone. In this alternative embodiment, the closed surface is in the form of an ellipsoid constructed from the strength values. Such strength surfaces are known in the art; see, for example, pp. 151–154 of the book *Bone Mechanics,* edited by Stephen C. Cowin, published by CRC Press, Boca Raton, Fla. in 1989, and incorporated by reference hereinto. The lengths of the three axes of the ellipsoid, as well as the center and orientation of the ellipsoid in stress space, are determined from the failure strengths in tension, compression and torsion. It should be understood that the invention disclosed herein may incorporate any of a number of strength surfaces and methods for their generation. For example, in yet another alternative embodiment, a more accurate three dimensional strength surface is constructed using the theory of Kelvin modes; this approach to strength surfaces is described in the publication "A Multidimensional Anisotropic Strength Criterion Based on Kelvin Modes, by Y. P. Arramon, M. M. Mehrabadi, D. W. Martin and S. C. Cowin, in *Int. J. Solids Structures,* Volume 37, pp. 2915–2935, 2000, and which is incorporated by reference hereinto. This more accurate surface construction depends upon the elastic constants and the strength values. It should be appreciated that in these alternative embodiments, the closed three-dimensional surfaces are obtained by taking advantage of the linear correlations, which exist, between elastic constants and strength for bone (see for example the publication "The Dependence of the Elasticity and Strength of Cancellous Bone on Apparent Density," by J. C. Rice, S. C. Cowin and J. A. Bowman, in *J. Biomechanics,* Volume 21, pp. 155–168, 1988). It should be additionally appreciated that in these alternative embodiments the closed three-dimensional strength surfaces are further processed to obtain the final estimate of strength. In a presently preferred alternative embodiment, this is accomplished by determining, for each type of physiologically possible mechanical loading to the whole bone, the anatomical site in the cancellous bone that will fail, and the magnitude of the physiologically possible mechanical loading that will cause failure. The worst load situation is determined by multiplying the inverse of the load magnitude by the probability of occurrence of its associated physiologically possible mechanical loading, and selecting the greatest number, to provide the estimate of bone strength. This is similar to a standard structural stress analysis of a machine part that is subjected to multiple types of loadings, a technique well known in the art of engineering. Finally, it should be appreciated that for the invention as disclosed herein bone strength may be estimated in a variety of ways, for example by an integration over the entire closed three-dimensional surface, or even include a which may or may not include the sub-step of deriving a closed three-dimensional surface.

It should also be appreciated that a quantitative measure of fracture risk may also be obtained according to the methods disclosed herein. In yet one further alternative preferred embodiment, the fracture risk associated with a bone at a bony locale in a living body is obtained by inverting the estimate of bone strength and normalizing the result to be between 0 and 1, although other methods may equivalently be used.

It should also be understood that the measurement of bone mineral density can be achieved in a number of ways. In the embodiments disclosed hereinabove, an MRI machine was used to obtain the density. However, the present invention should be understood to be embodied with a number of bone mineral density determination techniques, including for example, single photon absorptiometry, single energy x-ray absorptiometry, dual photon absorptiometry, dual energy x-ray absorptiometry, plain x-ray based densitometry and micro-computed x-ray tomography. Further, it should also be appreciated that stored anatomical data, e.g., a trabecular grain data base, can also serve as a source for the trabecular grain data required to implement the methods disclosed herein. Finally, trabecular grain can also be understood to be able to be determined from analysis of plain radiographs.

It will be seen that the described invention meets all stated objectives as to evaluation of the biomechanical status of bone tissue in vivo, with specific advantages that include but are not limited to the following:

(1) Determination of a full or partial set of anisotropic elastic constants;

(2) Inherent incorporation of architectural or structural information into the biomechanical estimates;

(3) Determination of overall strength and fracture risk;

(4) Relatively little additional complexity over current densitometric techniques, but with significant improvement in estimation of biomechanical properties, which should allow for improved and expanded health care delivery to the general population.

What is claimed is:

1. A method of non-invasively and quantitatively evaluating the biomechanical status of bone tissue in a bony locale of a body, as manifested through the quantity: a set of anisotropic elastic constants, which method comprises the steps of:

(a) determining a bone-mineral density associated with said bone tissue of said body;

(b) obtaining a principal-grain direction of said bone tissue; and (c) processing said bone-mineral density and said principal-grain direction to obtain said set of anisotropic elastic constants associated with said bone tissue at said bony locale of said body.

2. The method according to claim 1 wherein said determining a bone-mineral density associated with said bone tissue of said body is performed with a dual energy x-ray absorptiometry machine.

3. A method of non-invasively and quantitatively evaluating the biomechanical status of bone tissue in a bony locale of a body, as manifested through the quantity: bone strength, which method comprises the steps of:

(a) determining a bone-mineral density associated with said bone tissue of said body;

(b) obtaining a principal-grain direction of said bone tissue;

(c) processing said bone-mineral density and said principal-grain direction to obtain a set of anisotropic elastic constants associated with said bone at said anatomical site; and (d) processing said set of anisotropic elastic constants whereby to obtain said bone strength associated with said bone tissue at said bony locale of said body.

4. The method according to claim 3 wherein said determining a bone-mineral density associated with said bone tissue of said body is performed with a dual energy x-ray absorptiometry machine.

5. The method according to claim 3 wherein said processing said set of anisotropic elastic constants includes the sub-step of obtaining a three-dimensional strength surface.

6. A method of non-invasively and quantitatively evaluating the biomechanical status of bone tissue in a bony locale of a body, as manifested through the quantity: fracture risk, which method comprises the steps of:

(a) determining a bone-mineral density associated with said bone tissue of said body;

(b) obtaining a principal-grain direction of said bone tissue;

(c) processing said bone-mineral density and said principal-grain direction to obtain a set of anisotropic elastic constants associated with said bone tissue at said bony locale of said body; and (d) processing said set of anisotropic elastic constants whereby to obtain said fracture risk associated with said bone tissue at said bony locale of said body.

7. The method according to claim 6 wherein said determining a bone-mineral density associated with said bone tissue of said body is performed with a dual energy x-ray absorptiometry machine.

* * * * *